United States Patent [19]
Faul et al.

[11] Patent Number: 5,948,907
[45] Date of Patent: Sep. 7, 1999

[54] SYNTHESIS OF BISINDOLYLMALEIMIDES

[75] Inventors: Margaret Mary Faul, Zionsville; Leonard Larry Winneroski, Jr., Greenwood, both of Ind.

[73] Assignee: Eli Lilly and Company, Indianapolis, Ind.

[21] Appl. No.: 09/081,252

[22] Filed: May 19, 1998

Related U.S. Application Data

[62] Division of application No. 08/917,052, Aug. 22, 1997
[60] Provisional application No. 60/024,120, Aug. 23, 1996.

[51] Int. Cl.[6] ........................ C07D 498/22; C07D 487/22
[52] U.S. Cl. ........................ 540/469; 540/460; 540/472
[58] Field of Search .................................... 540/460, 469, 540/472, 474

[56] References Cited

U.S. PATENT DOCUMENTS

| | | | |
|---|---|---|---|
| 5,057,614 | 10/1991 | Davis et al. | 548/466 |
| 5,399,712 | 3/1995 | Hill | 578/455 |
| 5,541,347 | 7/1996 | Faul et al. | 552/105 |
| 5,559,228 | 9/1996 | Gillig et al. | 540/460 |
| 5,821,365 | 10/1998 | Jirousek et al. | 540/469 |

FOREIGN PATENT DOCUMENTS 0 540 956 A1  12/1993  European Pat. Off. .

OTHER PUBLICATIONS

Davis et al., Inhibitors of Protein Kinase C. 1. 2,3–Bisaryl-maleimides, *J. Med. Chem.* Jan. 1992, vol. 35, No. 1, pp. 177–184.

*Primary Examiner*—Richard L. Raymond
*Assistant Examiner*—Ann M. Kessinger
*Attorney, Agent, or Firm*—Paul R. Darkes

[57] ABSTRACT

The present invention provides for the reaction of optionally substituted indole-3-acetamides with optionally substituted methyl indole-3-glyoxyl reagent to prepare potent PKC inhibitors.

5 Claims, No Drawings

SYNTHESIS OF BISINDOLYLMALEIMIDES

This application is a divisional of U.S. Application Ser. No. 08/917,052, filed Aug. 22, 1997, and claims priority benefits of U.S. Provisional Application No. 60/024,120 filed Aug. 23, 1996.

FIELD OF THE INVENTION

The present invention relates to bis-indolylmaleimides which are useful as protein kinase C inhibitors. More specifically, the invention provides a robust and efficient process of preparing bis-indolylmaleimides. The compounds prepared by the process are useful in those disorders associated with abnormal levels of protein kinase C, including cardiovascular disease, diabetes mellitus and its complications, and cancer.

BACKGROUND OF THE INVENTION

The bis-indolylmaleimide subunit is present in a number of biologically active metabolites isolated from Streptomycetes including Staurosporine, (Tamaoki et al., *Biochem. Biophys. Res. Commun.* 135: 397–402 (1986); Gross et al., *Biochem. Pharmacol.* 40: 343–350 (1990)) and Rebeccamycin, (Steglich et al., *Angw Chem. Int. Ed. Engl.* 19:459 (1980)). The simplest members of this class of compounds are the arcyriarubins, a family of pigments produced by slime molds (Myxomycetes). Id. Bis-indolylmaleimides are selective inhibitors of PKC and show promise as a novel potential therapy for auto immune diseases (Bit, R. A. et al., *J. Med. Chem.* 361:21 (1993)). The bisindolylmaleimide GF109303X has been recognized as a PKC kinase selective agent, (Bit, R. A. et al., *Tetrahedron Letters* 34:5623 (1993)) as has the conformational restricted analog, Ro 32-0432 (Wilkinson, S. E., *J. Med. Chem.* 36:21 (1993)) and also N,N' bridged bisindolylmaleimide macrocycles (Jirousek et al., *J. Med. Chem.* 39 (14):2664–2671 (1996)).

Several methods are available in the literature to prepare the bis-indolylmaleimide framework including reaction of dihalomaleimides with indole Grignard reagents (Faul et al., *Synthesis* 12:1511 (1995) and Steglich, W. *Tetradron* 44: 2887 (1988)), oxidative coupling of indole-3-acetic acid trianions (Bergman et al., *Tetrahedron Letters* 28:1444 (1987)), and reaction of indolyl-3-glyoxyl chlorides with either indole-3-acetic acid in a Perkin condensation approach or with indole-3-acetimidates (Specter et al., *J. Am. Chem. Soc.* 76:6208 (1954); Davis, P. D., et al., *Tetrahedron Letters* 31:5201 (1990), Bit, R. A., *Tetrahedron Letters* 34:5623 (1993)) to prepare a bisindolylmaleic anhydride which is then converted to a bisindolylmaleimide in a two-step synthesis. Although all of these procedures can be utilized to prepare bisindolylmaleimides, one must use different procedures or multiple steps to prepare unsymmetrical vs. symmetrically substituted bisindolylmaleimides. Thus, there remains a need for a general and efficient method of preparing bis-indolylmaleimides.

The present invention provides a general and very efficient method for the synthesis of these substrates. The syntheses provides a flexibile and powerful methodology for the synthesis of bisindolylmaleimides.

SUMMARY OF THE INVENTION

This invention provides a process of preparing compounds of Formula I:

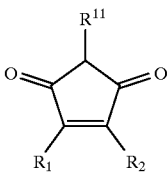

(I)

wherein: $R_1$ and $R_2$ independently are optionally substituted 3-indolyl and $R_{11}$ is H or $CH_3$; which comprises, reacting an optionally substituted indole-3-acetamide of the formula:

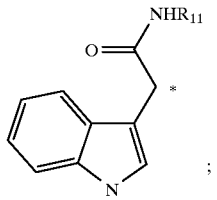

with optionally substituted indolyl-3-glyoxyl reagent of the formula:

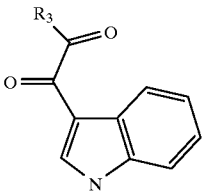

wherein:
   $R_3$ is I, Cl, Br, or $OR_4$; and
   $R_4$ is $C_1$–$C_4$ alkyl; in the presence of a base sufficiently strong to deprotonate the amide and methylene at the C-3 position of indolyl-3-acetamide.

DETAILED DESCRIPTION AND PREFERRED EMBODIMENTS

For purposes of the present invention, as disclosed and claimed herein, the following terms and abbreviations are defined as follows.

The term "halo" represents fluorine, chlorine, bromine, or iodine.

The term "alkyl" represents a cyclo, straight or branched chain alkyl group having from one to ten carbon atoms such as methyl, ethyl, n-propyl, isopropyl, cyclopropyl, n-butyl, isobutyl, sec-butyl, t-butyl and the like. A haloalkyl is one such alkyl substituted with one or more halo atoms, preferably one to three halo atoms. An example of a haloalkyl is trifluoromethyl. A $C_1$–$C_4$ alkyl is an alkyl limited to one to four carbon atoms. A $C_1$–$C_4$ alkoxy is a $C_1$–$C_4$ alkyl group covalently bonded by an —O-linkage.

The term "$C_1$–$C_4$ alkylene" represents a one to four carbon, straight alkylene moiety. Examples of $C_1$–$C_4$ alkylene include methylene, ethylene, trimethylene, methylethylene, tetramethylene, and the like. Similarly, a "$C_4$–$C_8$ alkylene" represents a four to eight carbon, straight alkylene moiety.

The term "aryl" represents a phenyl or naphthyl.

The term "alkali alkoxides" refers to bases, generally lithium, potassium, or sodium bases, of an alkoxide, generally a $C_1$–$C_4$ alkoxy. Alkali alkoxides therefore include potassium t-butoxide, sodium methoxide, sodium ethoxide.

The term "heterocycle" represents a stable, optionally substituted, saturated or unsaturated 5 or 6 membered ring, said ring having from one to four heteroatoms that are the same or different and that are selected from the group consisting of sulfur, oxygen, and nitrogen; and when the heterocycle contains two adjacent carbon atoms, the adjacent carbon atoms may be structured to form a group of the formula —CH=CH—; provided that (1) when the heterocyclic ring contains 5 members, the heteroatoms comprise not more than two sulfur or two oxygen atoms but not both; and (2) when the heterocyclic ring contains 6 members and is aromatic, sulfur and oxygen are not present. The heterocycle may be attached at any carbon or nitrogen which affords a stable structure.

The term "optionally substituted alkylene" optionally substituted heterocycle, "or optionally substituted aryl" refers to substitution by one to three groups independently selected from the group consisting of hydrogen, $C_1$–$C_4$ alkyl, $C_1$–$C_4$ alkoxy, $(CH_2)_m$ hydroxy, acetyl, carboxy, halo, haloalkyl, nitro, and $(CH_2)_m NR_5R_6$; wherein m is 0, 1, 2, or 3; and $R_5$ and $R_6$ are independently hydrogen, $C_1$–$C_4$ alkyl, phenyl, benzyl, or combine to the nitrogen to which they are bonded to form a saturated or unsaturated 5 or 6 member ring. Said groups particularly the hydroxy or amino, are optionally protected during the claimed reaction.

The term "leaving group" as used in the specification is understood by those skilled in the art. Generally, a leaving group is any group or atom that enhances the electrophilicity of the atom to which it is attached for displacement. Preferred leaving groups are triflate, mesylate, tosylate, imidate, chloride, bromide, and iodide.

The term "hydroxy protecting group" as used in the specification refers to one of the ether or ester derivatives of the hydroxy group commonly employed to block or protect the hydroxy group while reactions are carried out on other functional groups on the compound. The species of hydroxy protecting group employed is not critical so long as the derivatized hydroxy group is stable to the condition of subsequent reaction(s) and can be removed at the appropriate point without disrupting the remainder of the molecule. T. W. Greene and P. Wuts, *Protective Groups in Organic Synthesis*, John Wiley and Sons, New York, N.Y., 1991, provide a list of commonly employed protecting groups. Preferred hydroxy protecting groups are tert-butyldiphenylsilyloxy (TBDPS), tert-butyldimethylsilyloxy (TBDMS), triphenylmethyl (trityl), methoxytrityl, or an alkyl or aryl ester. A related term is "protected hydroxy," which refers to a hydroxy protecting group.

The term "amino protecting group" as used in the specification refers to substituents of the amino group commonly employed to block or protect the amino functionality while reacting other functional groups on the compound. The species of amino-protecting group employed is not critical so long as the derivatized amino group is stable to the condition of subsequent reaction(s) and can be removed at the appropriate point without disrupting the remainder of the molecule. T. W. Greene and P. Wuts, *Protective Groups in Organic Synthesis*, Chapter 7, provide a list of commonly employed protecting groups. See also J. W. Barton, *Protective Groups in Organic Chemistry*, Chapter 2. Preferred amino-protecting groups are t-butoxycarbonyl, pthalimide, a cyclic alkyl, and benzyloxycarbonyl. The related term "protected amino" defines an amino group substituted with an amino protecting group as defined.

The term "—NH protective groups" as used in the specification refers to sub-class of amino protecting groups that are commonly employed to block or protect the —NH functionality while reacting other functional groups on the compound. The species of protecting group employed is not critical so long as the derivatized amino group is stable to the condition of subsequent reaction(s) and may be removed at the appropriate point without disrupting the remainder of the molecule. T. W. Greene and P. Wuts, *Protective Groups in Organic Synthesis*, Chapter 7, page 362–385, provide a list of commonly employed protecting groups. Preferred —NH protecting groups are carbamate, amide, alkyl or aryl sulfonamide. The related term "protected —NH" defines a group substituted with an —NH protecting group as defined.

The notation "*" designates the methylene at the 3-position of indolyl-3-acetamide.

As previously noted, the invention provides a process of preparing compounds of Formula I:

(I)

wherein: $R_1$ and $R_2$ independently are optionally substituted 3-indolyl and $R_{11}$ is H or $CH_3$, which comprises, reacting an optionally substituted indolyl-3-acetamide with an optionally substituted indolyl-3-glyoxyl reagent in the presence of a base.

An advantage of the present invention is that the reaction is robust. Both the indole-3-acetamide and the indolyl-3-glyoxyl reagent may be optionally substituted with a wide variety of substituents recognized and disclosed in the prior art, provided that the substitution does not interfere with the reaction of the present invention. Preferred moieties are N-substituted, substituted on the fused 6-membered aromatic ring of the indolyl, and/or substituted at the 2-position of the indolyl. Also included are those bisindolylmaleimides wherein the N-substituents of the indolyl are linked together through a bridging moiety as hereinafter described. Substituents recognized as being desirable on a bisindolylmaleimide include, for example, those disclosed in U.S. Pat. Nos. 5,057,614, 5,380,746, EPO 470 490 A1, WP 91/13071, EPO 397 060 A2, EPO 384 349 A1, EPO 624 586, WO 94/14798, EP 0 657 458, U.S. Pat. No. 5,481,003, and U.S. Pat. No. 5,545,636, all of which are herein incorporated by reference.

Preferably, an optionally substituted indolyl-3-acetamide is a compound of the formula II:

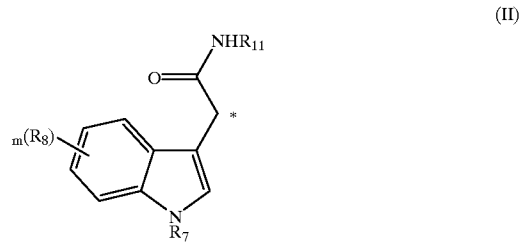

(II)

wherein:
$R_7$ is hydrogen, alkyl, haloalkyl, arylalkyl, $C_1$–$C_4$ alkoxyalkyl, optionally protected hydroxyalkyl, optionally protected aminoalkyl, monoalkylaminoalkyl, dialkylaminoalkyl, trialkylaminoalkyl, or COO($C_1$–$C_4$ alkyl);

$R_8$ is hydrogen, $C_1$–$C_4$ alkyl, $C_1$–$C_4$ alkoxy, $(CH_2)_m$ hydroxy, acetyl, carboxy, halo, haloalkyl, nitro, and $(CH_2)_m$ $NR_5R_6$; wherein m is 0, 1, 2, or 3; and $R_5$ and $R_6$ are independently hydrogen, $C_1$–$C_4$ alkyl, phenyl, benzyl, or combine to the nitrogen to which they are bonded to form a saturated or unsaturated 5 or 6 member ring.

Preferred moieties include those wherein $R_7$ is hydrogen, alkyl, optionally protected hydroxyalkyl, or optionally protected aminoalkyl; and $R_8$ is hydrogen. Other preferred compounds include those wherein $R_8$ is appendage at the 2-position of the indolyl and combines with $R_7$ to form a moiety of the formula (IIa):

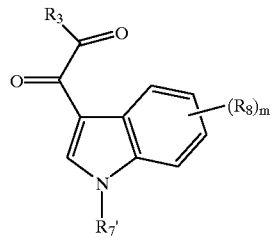

wherein X is an optionally substituted $C_1$–$C_4$ alkylene.

Preferably, X is methylene substituted with —$CH_2N(CH_3)_2$, a protected hydroxy or a protected amino.

Preferably, $R_{11}$ is H.

An optionally substituted indolyl-3-glyoxyl reagent is preferably a compound of the formula (III):

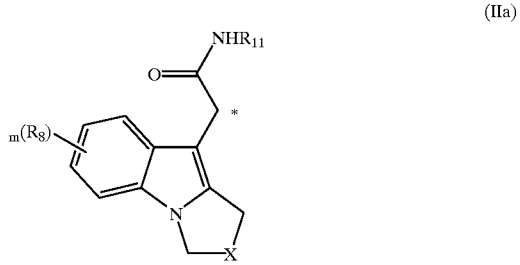

wherein:

$R_3$ is I, Cl, Br, or $OR_4$;

$R_4$ is $C_1$–$C_4$ alkyl;

$R_7$' is hydrogen, alkyl, haloalkyl, arylalkyl, alkoxyalkyl, optionally protected hydroxyalkyl, optionally protected aminoalkyl, monoalkylaminoalkyl, dialkylaminoalkyl, or trialkylaminoalkyl or COO($C_1$–$C_4$ alkyl);

$R_8$ is hydrogen, $C_1$–$C_4$ alkyl, $C_1$–$C_4$ alkoxy, $(CH_2)_m$ hydroxy, acetyl, carboxy, halo, haloalkyl, nitro, and $(CH_2)_m$ $NR_5R_6$; and m is 0, 1, 2, or 3.

Preferably, $R_3$ is Cl, Br, or $OR_4$ and most preferably $OR_4$. $R_7$' is preferably hydrogen, alkyl, haloalkyl, alkoxyalkyl, optionally protected hydroxyalkyl, optionally protected aminoalkyl, monoalkylaminoalkyl, or dialkylaminoalkyl.

Also included are compounds wherein $R_7$ and $R_7$' combine to form a bridging moiety linking the indolyl of the glyoxalyl reagent and the acetamide. Such compounds are of the formula (IV):

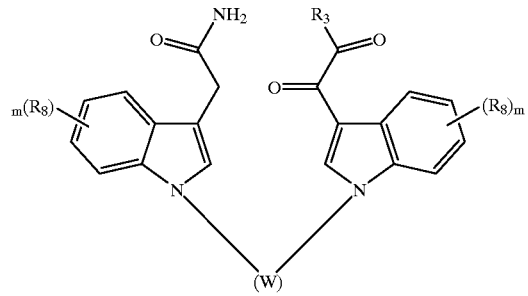

wherein W represents a $C_4$ to $C_8$ optionally substituted alkylene moiety, and optionally having an internal ether (—O—), amino (—NH—) or amide (—CONH—) linkage. Most preferred compounds are compounds wherein W has an internal ether linkage and are represented by Formula (IVa):

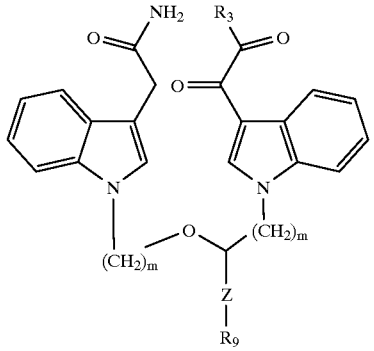

wherein Z is —$(CH_2)_p$—; $R_9$ is halo, protected hydroxy, protected amino, $NR_5R_6$, $NH(CF_3)$, or $N(CH_3)(CF_3)$; $R_5$ and $R_6$ are independently H or $C_1$–$C_4$ alkyl; p is 0, 1, or 2; and m is independently 2 or 3. Most preferred compounds of the Formula IVa are those wherein p is 1; and $R_5$ and $R_6$ are methyl.

Yet another preferred indolyl-3-acetamide is a compound of the formula:

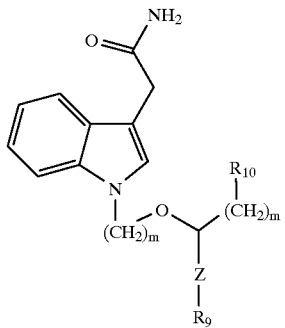

wherein:

m, Z, and $R_9$ are the same as previously defined, and $R_{10}$ is a leaving group, hydroxy, or protected hydroxy.

Compound (IVb) is preferably reacted with glyoxyl reagent (III) to yield a compound of the formula:

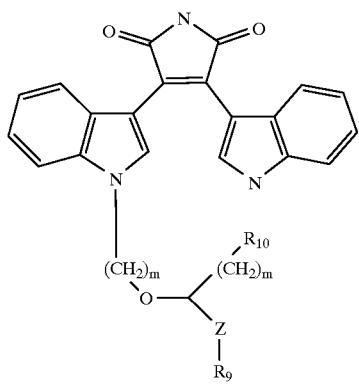

(IVc)

If a desired, compound IVc may be isolated from the reaction mixture; a macrocycle is then formed by the intramolecular alkylation of $R_{10}$ by techniques appreciated in the art and described in (EP 0 657 458 (Jun. 14, 1995)). Preferably, a macrocycle of the formula:

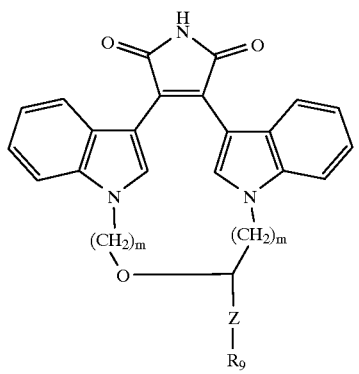

(IVd)

is prepared by reacting Compound IVc in the presense of base such as $K_2CO_3$, $Na_2CO_3$, NaOH, KOH, NaH, and $Cs_2Co_3$.

Similarly, the reaction may be carried out with substitution on the glyoxyl reagent. That is, an analogous compound of the Formula IVb:

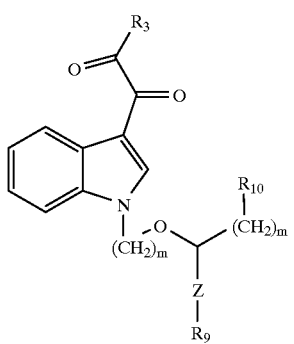

(IVb1)

may be reacted with an unsubstituted indolyl-3-acetamide to form a compound of IVa.

The reaction of glyoxyl reagent (IVb1) with indolyl-3-acetamide, or the reaction of indolyl-3-acetamide (IVb) with an unsubstituted indolyl-3-glyoxyl reagent may be controlled to yield macrocycle (IVd) in a one-step reaction. Presumably, N-alkylation to intermediate (IX) (below) takes advantage of intramolecular condensation to affect efficient maleimide formation. Both the bisindolylmaleimide and the macrocycle are formed in one step under mild conditions with no dimerization. For example, the following reaction

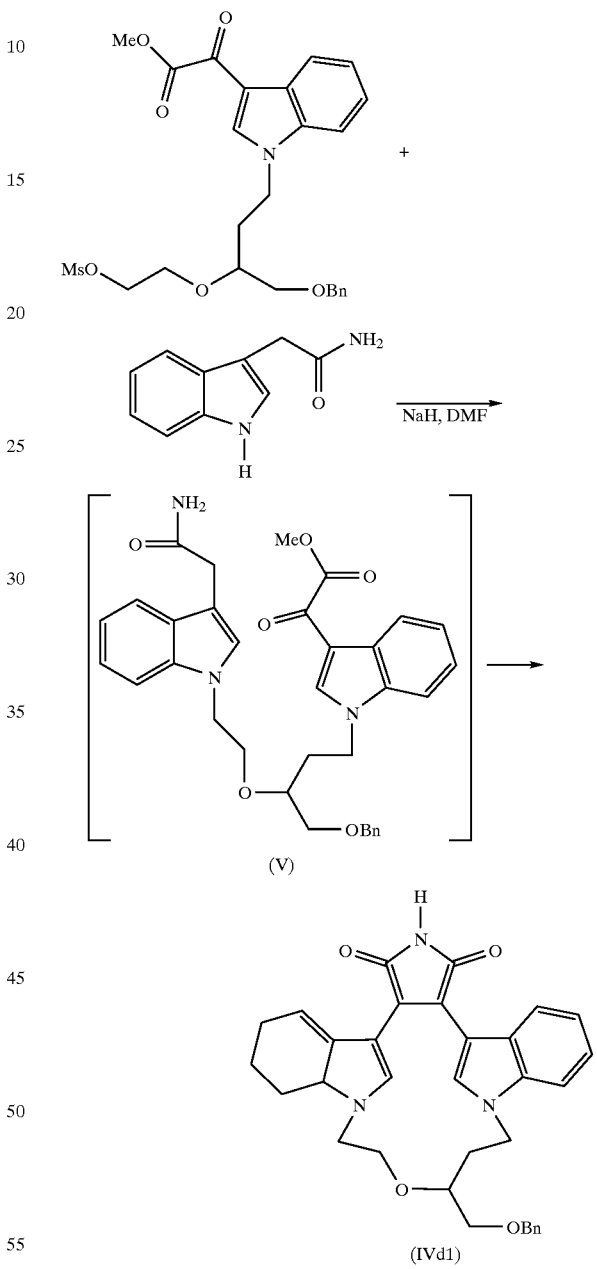

was carried out with about 5 equivalents of NaH at room temperature in about 20 volumes of DMF to yield (IVd1) in 58% yield. The reaction was unsuccessful when using NaH in THF under these conditions while potassium t-butoxide in DMF was also operable. Thus, a substituted or unsubstituted bis-indolylmaleimide macrocycle may be formed in an efficient one-stop reaction. Such a robust synthesis was previously unknown in the art.

It is recognized that various stereoisomeric forms of the compounds described herein may exist; compounds of the Formula (IVd) may contain a chiral carbon atom in the substituted alkylene moiety. The compounds are normally prepared as racemates and can conveniently be used as such, but individual enantiomers can be isolated or synthesized by the techniques described herein if so desired. Preparation of such racemates and individual enantiomers and mixtures thereof form part of the present invention.

The present invention is based on the discovery that an indole-3-acetamide reacts with an indolyl-3-glyoxyl reagent upon treatment with a base sufficiently strong to deprotonate the amide of the indolyl-3-acetamide and to deprotonate the methylene at the methylene carbon at the 3-position of the indolyl. Preferred bases are selected from the group consisting of alkali metal alkoxides, sodium hydride, lithium diisopropylamide, or n-butyllithium and are most preferably alkali alkoxides such as potassium tert-butoxide (KOBu$^t$). The reaction is carried out with a molar excess of base, preferably from about 0.5 to 10 equivalents of base, most preferably about 3.0 to 5.5 equivalents. However, one skilled in the art would recognize that the equivalents of base is dependent on the number of acidic hydrogens in the molecules.

The reaction may be carried out in an organic solvent which is inert under the conditions of the reaction. Such solvents include, but are not limited to, ether solvents such as tetrahydrofuran, tert-butyl methyl ether, ether, and dimethoxyethane; alcohol solvents such as ethanol or butanol; or polar solvents such as dimethylformide, dimethylsulfoxide, or acetonitrile. A preferred solvent is tetrahydrofuran. Alcohol solvents are least preferred due to the solvent's possible quenching effect on the base.

The reaction usually involves approximately equimolar amounts of the two reagents although other reagent equivalents are operative. The temperature of the reaction is preferably about 0° C. to about the reflux temperature of the reaction mixture.

The indolol-3-glyoxyl reagent utilized in this invention is prepared by conditions appreciated in the art. Generally, the glyoxyl reagent is prepared by techniques described in Feldman P. L., et al. *Synthesis-Stuttgart* 9: 735–37 (1986), Downie I. M. et al., *Tetrahedron* 49 (19): 4015–34 (1993), Rone N. et al. *Synthetic Commun* 25 (5): 681–90 (1995), Oikawa Y. et al. *Heterocycles* 4: 1859 (1976), DaSettimo *JOC* 35: 2546 (1970), and Rawal U. H. *Tetrahedron Lett.* 26: 6141 (1985), herein incorporated by reference. Preferably the glyoxyl reagent is prepared from an indole by sequential treatment of indole with oxalyl chloride followed by sodium methoxide (25% wt. solution in methanol) at low temperature (<-60° C.).

The indolyl-3-acetamide is prepared by conditions appreciated in the art or purchased from Aldrich Chemical Company, (Aldrich Chemical, Milwaukee, Wis., catalog, page 725 (1992–1993). Substitution to the acetamide is carried out by technique appreciated in the art and described in Rubottm G. et al., *Synthesis* 566 (1972), herein incorporated by reference.

Though not wishing to be limited to any technical explanation, applicants believe the mechanism of the claimed reaction is as illustrated in Scheme 1.

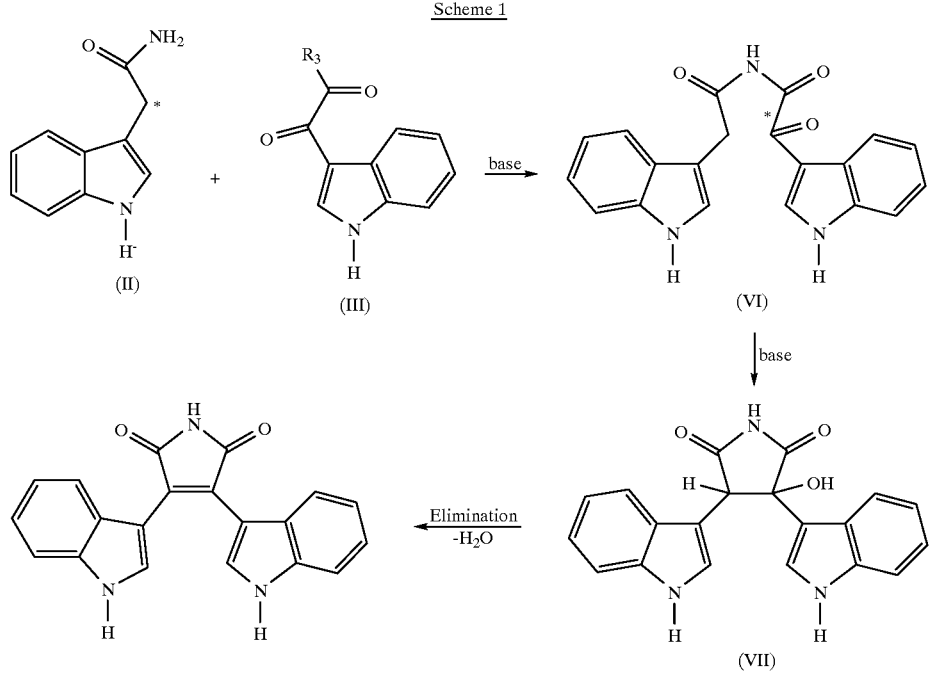

Scheme 1

Compound (VI) and (VII) (trans and cis) can be isolated from the reaction mixture. These intermediates have been characterized by NMR, mass spectroscopy, and IR. Elimination (dehydration of (VII) to Compound I) can be achieved with an acid or a base. Preferably HCl is used when the indole-3-acetamide is unsubstituted. When a substituted indole-3-acetamide is employed, the reaction is preferably quenched with excess base. Accordingly, an advantage of the present invention is that an indole containing acid sensitive functionality could be cyclized readily by placing the substitution on the indole-3-acetamide. Preferably, Compound (VII) is converted to the final product in the same pot by quenching the reaction with HCl.

When the indole-3-acetamide (II) is substituted complete elimination is achieved in about 1 to 5 hours to produce the bis-indolylmaleimide without the need to add acid. This elimination could be further enhanced by using more base, preferably 4 to 5 eq. of base, in the reaction which lead to complete cyclization in about 15 minutes to 1 hour. For example, acid sensitive ketal and trityl containing indole-3-acetamides may be cyclized with Compound III in one pot to give bis-indolylmaleimides in excess of 90% yield without the need to add an acid to quench the reaction and complete the elimination. Surprisingly, even hydroxyl and amino substituted indole-3-acetamides could be cyclized to give bis-indolylmaleimides in 98% and 84% yields respectively.

The following examples of the claimed syntheses demonstrate the flexibility and power of this methodology for the synthesis of bisindolylmaleimides. The examples are offered to illustrate the invention and are not to limit the scope of the invention to the following examples. In the following examples, the designation "NMR" or "MS" means that the structure was confirmed by NMR or mass spectroscopy.

GENERAL

Infrared spectra were recorded on a Perkin Elmer 781 spectrometer. $^1$H NMR spectra were recorded on a QE 300 MHz spectrometer at ambient temperature. Data are reported as follows: chemical shift in ppm from internal standard tetramethylsilane on the d scale, multiplicity (b=broad, s=singlet, d=doublet, t=triplet, q=quartet, qn=quintet and m=multiplet), integration, coupling constant (Hz) and assignment. $^{13}$C NMR were recorded on a QE 300 MHz (75.5 MHz) spectrometer at ambient temperature. Chemical shifts are reported in ppm from tetramethylsilane on the d scale, with the solvent resonance employed as the internal standard (deuterochloroform at 77.0 ppm and DMSO-$d_6$ at 39.5 ppm). Combustion analyses were performed by Eli Lilly & Company Microanalytical Laboratory. High resolution mass spectra were obtained on VG ZAB 3F or VG 70 SE spectrometers. Analytical thin layer chromatography was performed on EM Reagent 0.25 mm silica gel 60-F plates. Visualization was accomplished with UV light.

Preparation 1

1-Methyl-indole-3-acetamide

A solution of indole-3-acetonitrile (10.0 g, 64.0 mnol) in DMF (50 mL) was added dropwise to a suspension of sodium hydride (3.33 g, 83.3 mmol) in DMF (20 mL) at room temperature. The resultant mixture was stirred for 30 minutes and was cooled to 0°–5° C., and a solution of methyl iodide (13.63 g, 96.0 mmol) in DMF (30 mL) was added dropwise. The reaction was allowed to warm and stir at room temperature for 3 hrs. The reaction was worked up extractively using EtOAc (300 mL) and aqueous 0.5N HCl (400 mL) and the organic layer dried (MgSO$_4$) and solvent removed in vacuo to give 16.34 g (>100%) of crude alkylated product that was carried on without purification as follows. The oil was combined with tetrabutylammonium bromide (4.13 g, 12.8 mmol) in CH$_2$Cl$_2$ (100 mL) and was cooled in an ice bath before a 30% aqueous solution of hydrogen peroxide (33 mL) was added followed by an aqueous 20% weight solution of NaOH (26 mL). The reaction was allowed to warm to room temperature and stir for 21 hours before being worked up extractively with CH$_2$Cl$_2$ (650 mL), aqueous 1N HCl (500 mL) and water (500 mL). The organic layer was dried (MgSO$_4$) and solvent removed in vacuo to give a thick slurry to which was added hexanes (100 mL). This mixture was filtered using 1:1 CH$_2$Cl$_2$:hexanes (100 mL) as a rinse to give 8.45 g (70%) of the titled product after drying. NMR. MS (FD) m/z=188 (M$^+$, 100%). Anal. calc'd for C$_{11}$H$_{12}$N$_2$O C, 70.19; H, 6.43; N, 14.88. Found C, 70.02; H, 6.17; N, 14.99.

Preparation 2

1-(2,2-Dimethyl-1,3-dioxolanyl-4-ethyl)-3-indole-3 acetamide

A solution of indole-3-acetamide (13.5 g, 77.5 mmol) in DMF (50 mL) was added dropwise to a suspension of sodium hydride (4.3 g, 0.109 mole) in DMF (50 mL) at 0°–5° C. The resultant mixture was stirred for 1 hour in the ice bath and then 4-[2-p-toluenesulfonylethyl]-2,2-dimethyl-1,3-dioxolone (Tanis, S. P. et al., *J. Org. Chem.* 52: 819 (1987), 34.9 g, 0.116 mole) was added dropwise. The reaction was allowed to warm and stir at room temperature for 16 hrs., and the reaction was worked up extractively using EtOAc, brine and 5% aqueous LiCl, and the organic layer dried (MgSO$_4$), and solvent removed in vacuo to give an oil to which Hexanes:EtOAc (4:3) was added (225 mL), The product was crystallized and was isolated to give 19.4 g (83%) of product after drying. NMR. MS (FD) m/z=302 (M+, 100%). Analytical calculated for C$_{17}$H$_{22}$N$_2$O$_3$ C, 67.53; H, 7.33; N, 9.26. Found C, 67.72; H, 7.38; N, 9.31.

Preparation 3

1-(3-O'-Triphenylmethylpropyl)-indole-3-acetamide

A solution of indole-3-acetamide (5.00 g, 28.7 mmol) in DMF (25 mL) was added to a suspension of sodium hydride (1.61 g, 40.3 mmol) in DMF (25 mL) at room temperature under N$_2$. The resultant mixture was stirred 30 min. at room temperature and was then cooled to 0°–5° C. A solution of 3-bromo-1-(O'-triphenylmethyl)-propanol (16.4 g, 43.1 mmol) in DMF (40 mL) was added and the reaction was stirred for 16 hours at room temperature. The reaction was worked up extractively using EtOAc (700 mL) water (2× 500 mL) and brine (200 mL) and then dried (MgSO$_4$) and the solvent removed in vacuo to give 23.1 g of crude product which was purified by flash chromatography using 1:1 hexanes:acetone to give 12.45 g (91%) of product as an oil. A solid was crystallized by dissolving the oil in EtOH (50 mL) to yield 9.65 g (71%) of the titled product. NMR. MS (FD) m/z=474 (M$^+$, 100%). Analytical calculated for C$_{32}$H$_{30}$N$_2$O$_2$ C, 80.98; H. 6.37; N, 5.90. Found C, 80.84; H, 6.59; N, 5.62.

Preparation 4

1-(1-Hydroxypropyl)-indole-3-acetamide

A solution of 3-indolylacetonitrile (3.00 g, 19.2 mmol) in DMF (30 mL) was added dropwise to a suspension of sodium hydride (1.08 g, 27.0 mmol) in DMF (10 mL) at room temperature. The resultant mixture was stirred at room temperature for 30 min. before a solution of 3-bromopropylacetate (4.87 g, 26.9 mmol) in DMF (15 mL) was added. The reaction was stirred an additional 3 hours at room temperature before being worked up extractively with EtOAc (250 mL), aqueous 0.5N HCl (200 mL), water (200 mL) and brine (50 mL) and the solvent was removed in vacuo to give 6.91 g (>100%) of crude alkylated product which was converted to 1-(1-hydroxypropyl)-indole-3-acetamide without purification as follows. The oil was dissolved in tert-butanol (70 mL), treated with freshly powdered potassium hydroxide (85%, 12.7 g, 192 mmol) and the resultant mixture heated to a gentle reflux for 1 hr. The reaction mixture was then poured into ice and the acidity adjusted to pH~1 using aqueous 6N HCl (35 mL). The reaction was worked up extractively using EtOAc (300 mL), water (200 mL), brine (50 ml) and the organic layer dried (MgSO$_4$) and the solvent removed in vacuo to give a solid that was purified by flash chromatography using a 2:1 acetone:hexanes initially followed by 95:5 acetone:MeOH to give 2.73 g (61%) of 1-(1-Hydroxypropyl)-indole-3-acetamide. NMR. MS (FD) m/z=232 (M$^+$, 100%). Analytical calculated for C$_{13}$H$_{16}$N$_2$O$_2$ C, 67.22; H, 6.94; N, 12.06. Found C, 65.99; H. 7.24; N, 11.0.

Preparation 5

1-(Dimethylaminopropyl)-indole-3-acetamide

A suspension of 1-(methanesulfonylpropyl-indole-3-acetamide (1.0 g, 3.20 mmol) in THF (15 mL) was treated with a 40% aqueous solution of dimethylamine (13.5 mL, 0.108 mole) and the resultant reaction solution was capped and stirred at room temperature for 18 hours. The reaction was worked up extractively using EtOAc (50 mL), water (2× 50 mL) and brine (25 ml). The combined aqueous layers were back-extracted three times with EtOAc (3× 25 mL) and the combined organic layer dried (MgSO$_4$) and the solvent removed in vacuo to give 0.77 g (92%) of 1-(Dimethylaminopropyl)-indole-3-acetamide. NMR. MS (FD) m/z=259 (M$^+$, 100%).

Preparation 6

Methyl indolyl-3-glyoxylate

A solution of indole (2.0 g, 1.70 mmol) in Et$_2$O (20 mL) was cooled to 0°–5° C. under N$_2$ and oxalyl chloride (1.5 mL 1.70 mmol) was added dropwise at <5° C. The resultant yellow slurry was stirred 30 min. in the ice bath and was then cooled to −65° C. and a 25% wt. solution of sodium methoxide (7.8 mL, 3.4 mmol) was slowly added at <−58° C. The reaction was then allowed to warm to room temperature, water was added (10 mL), and the resultant mixture filtered. The solid was dried at room temperature to give 3.21 g (93%) of the titled compound. NMR. MS (FD) m/z=203 (M$^+$, 100%). Analytical calculated for C$_{11}$H$_9$NO$_3$ C, 65.02; H, 4.46; N, 6.89. Found C, 64.93; H, 4.25; N, 7.03.

Preparation 7

Methyl (1-methyl-indolyl-3)-glyoxylate

A solution of N-methylindole (2.0 g, 1.52 mmol) in Et$_2$O (20 mL) was cooled to 0°–5° C. under N$_2$ and oxalyl chloride (1.3 mL 1.52 mmol) was added dropwise at <5° C. The resultant yellow slurry was stirred 30 min. in the ice bath and was then cooled to −65° C. and a 25% wt. solution of sodium methoxide (7.0 mL, 3.04 mmol) was slowly added at <−58° C. The reaction was then allowed to warm to room temperature, water was added (10 mL), and the resultant mixture filtered and the solid dried at room temperature to give 2.93 g (89%) of the titled compound. NMR. MS (FD) m/z=217 (M$^+$, 100%). Analytical calculated for C$_{12}$H$_{11}$NO$_3$ C, 66.35; H, 5.10; N, 6.45. Found C, 66.29; H, 5.39; N, 6.65.

Preparation 8

3-Bromopropyl acetate

Acetic anhydride (74.7 mL, 0.792 mole) was added to a 0°–5° C. solution of 3-bromo-1-propanol (100 g, 0.720 mole) and 4-dimethylaminopyridine (8.79 g, 72.0 mmol) in CH$_2$Cl$_2$ (500 mL). The reaction was warmed to room temperature for 4 hours and then the reaction was worked up extractively with CH$_2$Cl$_2$ (200 mL), aqueous 1N HCl (2× 300 mL), saturated NaHCO$_3$ (2× 300 mL) and brine (200 mL) and the solvent was removed in vacuo to give 128.52 g (99%) of the above titled compound. NMR. MS (FD) m/z=180 (M$^+$, 100%). Analytical calculated for C$_5$H$_9$O$_2$Br C, 33.17; H, 5.01. Found C, 33.69; H, 5.09.

Preparation 9

3-Bromo-1-(O'-triphenylmethyl) propanol

Trityl chloride (109 g, 0.391 mole) was dissolved in CH$_2$Cl$_2$ (500 mL) and cooled to 0°–5° C. under N$_2$ and triethylamine (59.4 mL, 0.426 mole) was added followed by a solution of 3-bromo-1-propanol (49.4 g, 0.355 mole) in CH$_2$Cl$_2$ (100 mL). The reaction mixture was allowed to warm and stir at room temperature for 4 hrs. The reaction was worked up extractively using CH$_2$Cl$_2$ (150 mL), water (500 mL) and brine (150 mL) and then dried (MgSO$_4$) and the solvent removed in vacuo to give 144.6 g of crude product which was purified by flash chromatography using a gradient of 2:1 to 1:1 hexanes:CH$_2$Cl$_2$ to give 105.7 g (78%) of the above titled compound as a solid. NMR. MS (FD) m/z=380 (M$^+$, 100%). Analytical calculated for C$_{22}$H$_{21}$OBr C, 69.30; H, 5.55. Found C, 69.10; H, 5.48.

Preparation 10

1-(Methanesulfonylpropyl)-indole-3-acetamide

Methanesulfonyl chloride (0.67 mL, 14.5 mmol) was added dropwise to a 0°–5° C. solution of 1-(1-hydroxypropyl)-indole-3-acetamide (1.68 g, 7.23 mmol) and triethylamine (1.41 mL, 10.1 mmol) in CH$_2$Cl$_2$ (20 mL) under N$_2$. The reaction was stirred 30 minutes in the ice bath and then the reaction was worked up extractively using CH$_2$Cl$_2$ (200 mL), water (100 mL), aqueous saturated NH$_4$Cl (100 mL) and brine (50 ml), and the organic layer dried (MgSO$_4$) and the solvent removed in vacuo to give a solid that was triturated in THF (15 mL) and filtered to give 1.58 g (71%) of the above titled compound after drying. NMR. MS (FD) m/z=310 (M$^+$, 100%). Analytical calculated for C$_{14}$H$_{18}$N$_2$O$_3$S C, 54.18; H, 5.85; N, 9.03. Found C, 54.64; H, 5.98; N, 8.97.

Preparation 11

1-(Triphenylmethoxy)-2-(2-(indole-3-acetamide)-oxy)-4-butanetriol 1,2-(dimethylacetonide)-4-butanetriol (9.5 g, 65.07 mmol) was taken up in 100 ml CH$_2$Cl$_2$ at room temperature. Imidazole (8.85 g, 130.15 mmol, 2.0 eq) was added followed by t-butyldimethyl-silyl chloride (16.99 g, 61.81 mmol, 0.95 eq). The reaction was stirred at room temperature for 4 hours. It was quenched with NH$_4$Cl solution, washed with brine, dried over MgSO$_4$, and evaporated to an oil. This oil was taken up in 80% aqueous acetic acid and stirred at room temperature for 24 hours. It was quenched with water and diluted with CH$_2$Cl$_2$. The resulting organic layer was washed with saturated NaHCO$_3$ solution and water and dried over MgSO$_4$ before evaporating to an oil which was purified by column chromatography to give 14.2 g 1,2,4-(t-Butyldiphenylsilyloxy)-butanetriol as a clear oil (71% yield).

1,2,4-(t-Butyldiphenylsilyloxy)-butanetroil (28.0 g, 81.4 mmol) was taken up in 400ml CH$_2$Cl$_2$ at room temperature.

Triethylamine (13.6 ml, 97.7 mmol, 1.2 eq) was added followed by trityl chloride (25.0 g, 89.5 mmol, 1.1 eq). The reaction was stirred at room temperature for 24 hours. It was quenched with NH$_4$Cl solution. The resulting organic layer was washed with brine and dried over MgSO$_4$ before evaporating to an oil which was purified by column chromatography (7/1 hexane/EtOAc) to give 40.9 g 1-(Triphenylmethoxy)-2,4-(t-butyldiphenylsilyloxy)-butanetriol as a clear oil (96% yield).

NaH (5.0 g, 124.2 mmol, 1.4 eq) was taken up in 100 ml THF. 1-(Triphenylmethoxy)-2,4-(t-butyldiphenylsilyloxy)-butanetriol (52.0 g, 88.7 mmol) was taken up in 400 ml THF and added to the reaction. The reaction was heated at 45° C. for 1 hour and then allyl bromide (13.8 ml, 159.7 mmol, 1.8 eq) was added dropwise. The reaction was heated at 45° C. for 12 additional hours. It was quenched with NH$_4$Cl solution. The resulting organic layer was washed with brine and dried over MgSO$_4$ before evaporating to an oil which was purified by column chromatography (9/1 hexane/EtOAc) to give 44.8 g 1 -(Triphenylmethoxy)-2-(2-pentenoxy)-4-(t-butyldiphenylsilyloxy)-butanetriol as a clear oil (81% yield). 1-(Triphenylmethoxy)-2-(2-pentenoxy)-4-(t-butyldiphenylsilyloxy)-butanetriol (3.6 g, 5.76 mmol) was taken up in 30 ml 1/1 CH$_2$Cl$_2$/MeOH and cooled to –50° C. Ozone was bubbled into the reaction for 30 min, monitored by the color change of sudan red indicator. Still at –50° C. sodium borohydride (0.43 g, 11.52 mmol, 2.0 eq) was added and the reaction was slowly allowed to come to room temperature overnight. It was quenched with NH$_4$Cl solution and the resulting organic layer was further washed with brine and dried over MgSO$_4$ before evaporating to an oil which was purified by column chromotography (3/1 hexane/EtOAc) to give 2.3 g 1-(Triphenylmethoxy)-2-(2-hydroxyethoxy)-4-(t-butyldiphenylsilyloxy)-butanetriol as a clear oil (63% yield).

1-(Triphenylmethoxy)-2-(2-hydroxyethoxy)-4-(t-butyldiphenylsilyloxy)-butanetriol (18.6 g, 30.0 mmol) was taken up in 200 ml CH$_2$Cl$_2$ and cooled to –5° C. Triethylamine (5.2 ml, 37.5 mmol, 1.25 eq) was added and then methanesulfonyl chloride (2.8 ml, 36.0 mmol, 1.2 eq) was added dropwise, maintaining the temperature below 0° C. The reaction was stirred at –5° C. for 30 min. It was quenched with NH$_4$Cl and the resulting organic layer was washed with brine and dried over MgSO$_4$ before evaporating to give 19.7 g 1-(Triphenylmethoxy)-2-(2-(methanesulfonyloxy)ethoxy)-4-(t-butyldiphenylsilyloxy)-butanetriol as a light yellow oil (96% yield). 60% NaH in mineral oil (5.18 g, 129 mmol, 1.5 eq) was taken up in 400 ml DMF and cooled to 0° C. A solution of indole-3-acetamide (22.6 g, 129 mmol, 1.5 eq) in 325 ml DMF was added slowly, maintaining a temperature below 0° C. The reaction was then allowed to come to room temperature and stir for 2 hrs. It was recooled to 0° C. and a solution of 1 -(Triphenylmethoxy)-2-(2-(methanesulfonyloxy)ethoxy)-4-(t-butyldiphenylsilyloxy)-butanetriol (61.3 g, 86.4 mmol) in 500 ml DMF (20 vols total) was added slowly, maintaining the temperature below 0° C. The reaction was allowed to stir at 0° C. for 1 hour and them left to come to room temperature and stir overnight. It was quenched with NH$_4$Cl solution, diluted with EtOAc, and the resulting organic layer was washed several times with water to remove DMF. It was then dried by washing with brine, drying over MgSO$_4$, and evaporating to give 7=1-(Triphenylmethoxy)-2-(2-indole-3-acetamide)oxy)-4-(t-butyldiphenylsilyloxy)-butanetriol as a dark brown oil which was carried on without further purification. (TY=68.0 g).

1-(Triphenylmethoxy)-2-(2-(indole-3-acetamide)oxy)-4-(t-butyldiphenylsilyloxy)-butanetriol (68.0 g, 129 mmol) was taken up in 100 ml of a 1M solution of tetrabutylammonium flouride in THF. The reaction was stirred at room temperature for 6 hrs. It was quenched with water and diluted with EtOAc to improve separation. The resulting organic layer was washed with brine, dried over MgSO$_4$, and evaporated to a brown oil which was purified by column chromatography (1/1 hexane/acetone to 100% acetone) to yield 26.0 g of the titled compound as a foamy off-white solid (55%—2 step yield).

EXAMPLE 1

3,4-(3-indolyl)-1H-pyrrole-2,5-dione

A suspension of indole-3-acetamide (1.00 g, 5.74 mmol) and methyl indolyl-3-glyoxylate (1.28 g, 6.30 mmole) in THF (10 mL) was treated with a 1 molar solution of potassium tert-butoxide in THF (17.2 mL, 17.2 mmol) at room temperature under N$_2$. The resultant dark reaction mixture was stirred 3 hrs. at room temperature and was then treated with concentrated (37%) HCl (8 mL) allowing the reaction to exotherm. The reaction was worked up extractively using EtOAc (125 mL), water (2× 100 mL), brine (25 ml) and the organic layer dried (MgSO$_4$) and solvent removed in vacuo to give a solid that was purified by flash chromatography using a gradient of 2:1 to 1:1 hexanes:EtOAc to give 2.04 g (100%) of arcyriarubin A [1.28 g (68%) when using glyoxylyl chloride]. 3,4-(3-indolyl-1H-pyrrole-2,5-dione could also be recrystallized from EtOH to give a stiochiometric ethanol monosolvate in high purity (>99%) and yield (88%). NMR. MS (FD) m/z=327 (M$^+$, 100%). Analytical calculated for C$_{22}$H$_{19}$N$_3$O$_3$ C, 70.76; H, 5.13; N, 11.25. Found C, 70.97; H, 5.22; N, 11.12.

EXAMPLE 2

3-[(1-Methyl)-3-indolyl]-4-(3-indolyl)-1H-pyrrole-2,5-dione

Method 1

A suspension of 1-methyl-indole-3-acetamide (1.00 g, 5.31 mmol) and methyl indolyl-3-glyoxylate (1.30 g, 6.40 mmole) [or 1.32 g, 63.6 mmol of indole-3-glyoxyl chloride] in THF (10 mL) was cooled in an ice bath under N$_2$ and then treated with a 1 molar solution of potassium tert-butoxide in THF (15.9 mL, 15.9 mmol). The resultant dark reaction mixture was stirred 5 minutes in the ice bath and 2.5 hrs. at room temperature and was then treated with concentrated (37%) HCl (8 mL) allowing the reaction to exotherm. The reaction was worked up extractively using EtOAc (150 mL), water (100 mL), brine (25 ml) and the organic layer dried (MgSO$_4$) and the solvent removed in vacuo to give a solid that was purified by flash chromatography using a gradient of 2:1 to 1:1 hexanes:acetone to give 1.66 g (92%) of the titled compound [1.38 g (76%) obtained upon using glyoxyl chloride].

Method 2

A suspension of indole-3-acetamide (1.00 g, 5.74 mmol) and methyl-(1-methyl-indolyl-3-glyoxylate (1.50 g, 6.91 mmole) in THF (10 mL) was cooled in an ice bath under N$_2$ and then treated with a 1 molar solution of potassium tert-butoxide in THF (17.2 mL, 17.2 mmol). The resultant dark reaction mixture was stirred 5 minutes in the ice bath and 2.5 hrs. at room temperature and was then treated with conc. (37%) HCl (8 mL) allowing the reaction to exotherm. The reaction was worked up extractively using EtOAc (150 mL), water (100 mL), brine (25 ml) and the organic layer dried (MgSO$_4$) and the solvent removed in vacuo to give a solid that was purified by flash chromatography using a gradient of 2:1 to 1:1 hexanes:acetone to give 1.71 g (87%) of the titled compound. NMR. MS (FD); m/z=341 (M$^+$, 100%). Analytical calculated for $C_{21}H_{15}N_3O_2$ C, 73.89; H, 4.43; N, 12.31. Found C 73.31; H 4.57; N 12.27.

EXAMPLE 3

3,4-[(1-Methyl)-3-indolyl]-1H-pyrrole-2,5-dione

A suspension of 1-methyl indole-3-acetamide (1.0 g, 5.31 mmol) and methyl (1-methyl-indol-3-yl)-glyoxylate (1.38 g, 6.35 mmole) in THF (10 mL) was treated with a 1 molar solution of potassium tert-butoxide in THF (15.9 mL, 15.9 mmol) at room temperature under $N_2$. The resultant reaction slurry was stirred 2 hrs. at room temperature and was quenched with 1N HCl (25mL). The product precipitated and was isolated by filtration after 15 minutes to give 1.88 g (99%) the titled compound. NMR. MS (FD) m/z=355 (M$^+$, 100%). Analytical calculated for $C_{22}H_{17}N_3O_2$ C, 74.35; H, 4.82; N, 11.82. Found C, 74.25; H, 5.03; N, 11.55.

EXAMPLE 4

3-[1-(2,2-Dimethyl-1,3-dioxolanyl-4-ethyl)-3-indolyl]-4-(3-indolyl)-1H-pyrrole-2,5-dione A suspension of 1-(2,2-dimethyl-1,3-dioxolanyl-4-ethyl)-3-indole-3-acetamide (1.00 g, 3.31 mmol) and methyl indole-3-glyoxylate (0.81 g, 3.99 mmol) in THF (10 mL) was cooled in an ice bath under $N_2$ and then treated with a 1 molar solution of potassium tert-butoxide in THF (14.9 mL, 14.9 mmol). The resultant dark reaction mixture was stirred 5 minutes in the ice bath and 1 hr. 15 min. at room temperature. The reaction was worked up extractively using EtOAc (125 mL), water (2× 100 mL), brine (25 ml) and the organic layer dried (MgSO$_4$) and the solvent removed in vacuo to give a solid that was purified by flash chromatography using a gradient of 2:1 to 1:1 hexanes:EtOAc to give 1.41 g (93%) of the titled compound. NMR. MS (FD) m/z=455 (M$^+$, 100%). Analytical calculated for $C_{27}H_{25}N_3O_4$ C, 71.19; H, 5.53; N, 9.23. Found C, 70.32; H, 5.72; N, 8.81.

EXAMPLE 5

3-[1-(3-O'-Triphenylmethylpropyl)-3-indolyl]-4-(3-indolyl)-1H-pyrrole-2,5-dione

A suspension of 1-(3-O'-triphenylmethylpropyl)-indole-3-acetamide (1.00 g, 2.10 mmol) and methyl indolyl-3-glyoxylate (0.51 g, 2.51 mmole) in THF (10 mL) was cooled in an ice bath under $N_2$ and then treated with a 1 molar solution of potassium tert-butoxide in THF (6.30 mL, 6.30 mmol). The resultant dark reaction mixture was stirred 5 minutes in the ice bath and 2 hrs. at room temperature. The reaction was worked up extractively using EtOAc (125 mL), water (100 mL), brine (25 ml) and the organic layer dried (MgSO$_4$) and the solvent removed in vacuo to give a solid that was purified by flash chromatography using 1:1 hexanes:acetone to give 1.20 g (91%) of the titled compound. NMR. MS (FD) m/z=627 (M$^+$, 100%). Analytical calculated for $C_{42}H_{33}N_3O_3$ C, 80.36; H, 5.29; N, 6.69. Found C, 79.35; H, 5.67; N, 6.29.

EXAMPLE 6

3-[1-(3-Hydroxypropyl)-3-indolyl]-4-(3-indolyl)-1H-pyrrole-2,5-dione

Method 1

A suspension of 1-(1-hydroxypropyl)-indole-3-acetamide (1.00 g, 2.10 mmol) and methyl indolyl-3-glyoxylate (0.51 g, 2.51 mmole) in THF (10 mL) was cooled in an ice bath under $N_2$ and then treated with a 1 molar solution of potassium tert-butoxide in THF (6.30 mL, 6.30 mmol). The resultant dark reaction mixture was stirred 5 minutes in the ice bath and 2 hrs. at room temperature and was then treated with conc. (37%) HCl (8 mL) and heated to reflux for 1 hr to detritylate the alcohol. The reaction was worked up extractively using EtOAc (125 mL), water (100 mL), brine (25 ml) and the organic layer dried (MgSO$_4$) and the solvent removed in vacuo to give a solid that was purified by flash chromatography using 1:1 hexanes:acetone to give 0.66 g (82%) of the titled compound.

Method 2

A solution of 1-(1-hydroxypropyl)-indole-3-acetamide (1.56 g, 6.71 mmol) and methyl indolyl-3 glyoxylate (2.73 g, 13.4 mmol) in THF (15 mL) was cooled in an ice bath under $N_2$ and then treated with a 1 molar solution of potassium tert-butoxide in THF (26.9 mL, 26.9 mmol). The resultant dark reaction mixture was stirred 5 minutes in the ice bath and 3 hrs. at room temperature and was quenched with conc. (37%) HCl (10 mL). The reaction was worked up extractively using EtOAc (300 mL), water (2× 200 mL), brine (50 ml) and the organic layer dried (MgSO$_4$), and the solvent removed in vacuo to give a solid that was purified by flash chromatography using a gradient of 2:1 to 1:1 hexanes:acetone to give 2.55 g (100%) of titled compound. NMR. MS (FD) m/z=385 (M$^+$, 100%). Analytical calculated for $C_{23}H_{19}N_3O_3$ C, 71.67; H, 4.97; N, 10.90. Found C, 71.08; H, 5.17; N, 10.32.

EXAMPLE 7

3-[1-(3-Dimethylaminopropyl)-3-indolyl]-4-(3-indolyl)-1H-pyrrole-2,5-dione

Method 1

A suspension of 1-(Dimethylaminopropyl)indole-3-acetamide (0.60 g, 2.31 mnol) and methyl indolyl-3-glyoxylate (0.94 g, 4.63 mmol) in THF (10 mL) was cooled in an ice bath under $N_2$ and then treated with a 1 molar solution of potassium tert-butoxide in THF (9.3 mL, 9.30 mmol). The resultant dark reaction mixture was stirred 5 minutes in the ice bath and 3 hrs. at room temperature. The reaction was worked up extractively using EtOAc (100 mL), water (2× 75 mL), brine (25 ml) and the organic layer dried (MgSO$_4$) and the solvent removed in vacuo to give a 1.13 g of a foam. Acetone (8 mL) was added to dissolve the foam and the product crystallized out and was isolated by filtration to give 0.80 g (84%) of the titled compound after drying.

Method 2

A suspension of 3-[1-methanesulfonylpropyl)-3-indolyl]-4-(3-indolyl)-1H-pyrrole-2,5-dione (70.39 g, 0.152 mole) in THF (1015 mL) was treated with a 40% aqueous solution of dimethylamine (423 mL, 3.37 moles) and the solids dissolved immediately to give a solution which was stirred at room temperature for 16 hrs. The reaction was worked up extractively with CH$_2$Cl$_2$ (1500 mL) and water (2× 1000 mL) and the solvent was removed in vacuo to give 59.98 g (96%) of the-titled compound. NMR. MS (FD) m/z=412 (M$^+$, 100%). Analytical calculated for $C_{25}H_{24}N_4O_2$ C, 72.80; H, 5.87; N, 13.58. Found C, 71.80; H, 6.31; N, 12.93.

EXAMPLE 8

3-[1 -(Methanesulfonylpropyl)-3-indolyl]-4-(3-indolyl)-1H-pyrrole-2,5-dione

A suspension of 3-[1-(3-Hydroxypropyl)-3-indolyl]-4-(3indolyl)-1H-pyrrole-2,5-dione (41.84 g, 0.109 mole) in CH$_2$Cl$_2$ (1200 mL) was treated with pyridine (26.3 mL, 0.326 mole) and then methanesulfonic anhydride (22.69 g, 0.130 mole) and the reaction was stirred for 2.5 hrs at room temperature under N$_2$. The reaction was then worked up extractively using aqueous 0.1N HCl (3260 mL), water (1500 mL) and brine (500 mL) and the organic layer dried (MgSO$_4$) and the solvent removed in vacuo to give 49.96 g (99%) of solid the titled compound. NMR. MS (FD) m/z= 464 (M$^+$, 100%). Analytical calculated for C$_{24}$H$_{21}$N$_3$O$_5$S C, 62.19; H, 4.57; N, 9,07; S, 6.92. Found C, 61.52; H, 4.72; N, 8.74; S, 6.88.

EXAMPLE 9

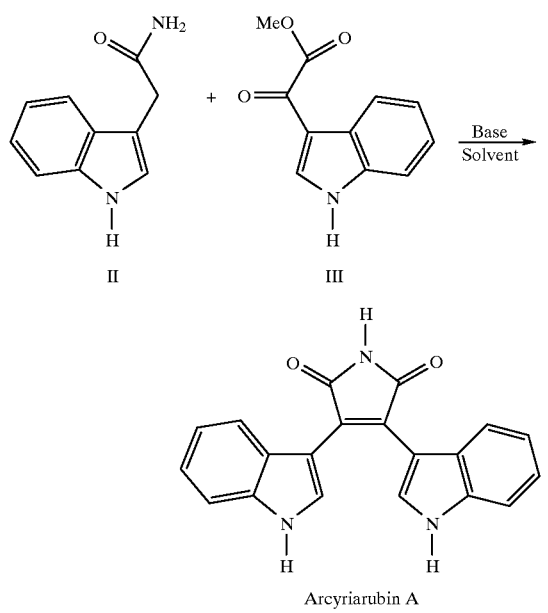

Arcyriarubin A

TABLE I

Effect of Solvent, Base and Addition (Add$^n$) Mode

| Entry | Solvent | Base (Eq.) | Eq. of III | Add$^n$ Mode[1] | Yield (%)[2] |
|---|---|---|---|---|---|
| 1 | THF | KOBu$^t$ (5.5) | 1.2 | A | 100 |
| 2 | THF | KOBu$^t$ (5.5) | 1.2 | B | 100 |
| 3 | THF | KOBu$^t$ (3.0) | 1.1 | A | 100 |
| 4 | DMF | KOBu$^t$ (4.5) | 1.1 | B | 36 |
| 5 | THF | NaH (3.5) | 1.2 | B | 56 |
| 6 | THF | NaH (3.0) | 1.2 | A | 39 |
| 7 | DMF | NaH (3.5) | 1.2 | B | 31 |
| 8 | THF | Et$_3$N (3.0) | 1.2 | A | no rxn. |
| 9 | Toluene | NaOH/TBAB | 2.0 | — | no rxn. |
| 10 | Water | NaOH/TBAB | 2.0 | — | no rxn. |

[1]Addition mode A = base added to reagents; addition mode B = reagents added to base.
[2]Chromatography yields.

EXAMPLE 10

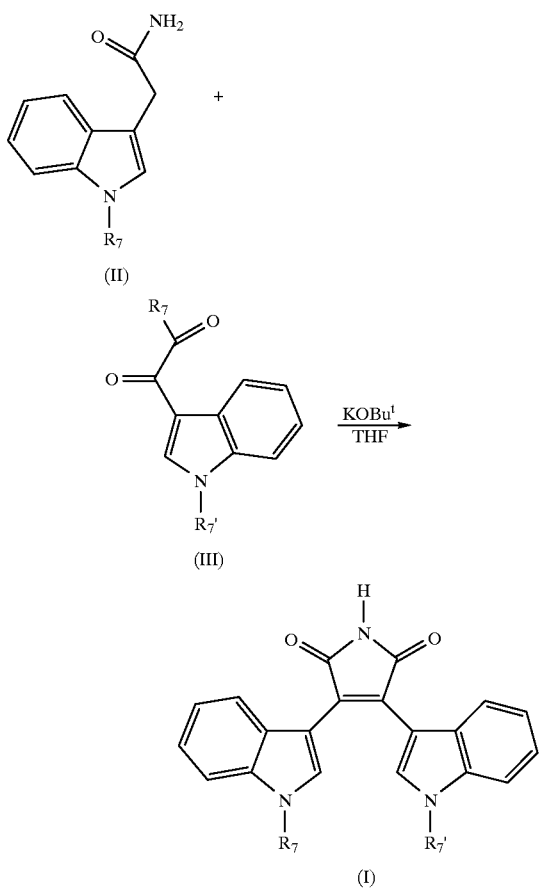

To determine the scope of this reaction, a series substituted indole-3-acetamides were prepared and reacted with substituted indolyl-3-glyoxy reagent under the conditions of 3 eq. of KOBU$^t$, 1.2 eq. indolyl-3-glyoxylates in THF. Reaction of unsubstituted indole-3-acetamide with unsubstituted indolyl-3-glyoxyl chloride gave a lower yield (68%) than obtained upon using the corresponding methyl glyoxylate ester (Table II, entries 1–2). In addition to giving higher yields, the ester was also superior to the glyoxyl chloride due to the fact that the compound is more stable to storage and could be analyzed by reverse phase HPLC.

TABLE II

Macrocyclization Results

| Entry | R$_7$ | R$_3$ | R$_7'$ | Yield (%)[1] |
|---|---|---|---|---|
| 1 | H | OMe | H | 100 |
| 2 | H | Cl | H | 68 |
| 3 | CH$_3$ | OMe | H | 92 |
| 4 | CH$_3$ | CL | H | 76 |
| 5 | H | OMe | CH$_3$ | 87 |
| 6 | CH$_3$ | OMe | CH$_3$ | 99[2] |
| 7 | 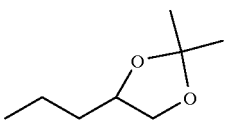 | OMe | H | 93[3] |

TABLE II-continued

Macrocyclization Results

| Entry | R$_7$ | R$_3$ | R$_7$' | Yield (%)[1] |
|---|---|---|---|---|
| 8 | ~~~OTrityl | OMe | H | 91 |
| 9 | ~~~OH | OMe | H | 62 |
| 10 | ~~~OH | OMe | H | 100[4] |
| 11 | ~~~N(Me)$_2$ | OMe | H | 72 |
| 12 | ~~~N(Me)$_2$ | OMe | H | 84[4] |

[1] Chromatography yields.
[2] Product isolated directly from reaction pot after quench with aqueous 1N HCl.
[3] Reaction run with 4.5 eq. base.
[4] Reaction repeated using 4.0 eq. base and 2.0 eq (III).

EXAMPLE 11

10,11,14,15-Tetrahydro-13-[(triphenylmethoxy)methyl]-4,9:16,21-dimetheno-1H, 13H-dibenzo[E.K]pyrrolo[3,4-H][1,4,13]oxadiaza-cyclohexadecine-1,3(2H)-dione 1-(Triphenylmethoxy)-2-(2-(indole-3-acetamide)-oxy)-4-butanetriol (24.9 g, 45.3 mmol) was taken up in 250 ml THF and indole-3-methyl glyoxylate (18.4 g, 90.7 mmol, 2.0 eq) was added. The slurry was cooled to 0° C. A 1M solution of KOBu$^t$ in THF (181 ml, 181 mmol, 4.0 eq) was added slowly. The light brown reaction mixture rapidly turned red and was allowed to come to room temperature and stir overnight. It was quenched with NH$_4$Cl solution and diluted with EtOAc. The resulting organic layer was washed with water, brine, dried over MgSO$_4$, and filtered through a 1 in. thick layer of silica gel to remove baseline acid before evaporating to yield 31.6 g 3-[1-[2-[1-(Triphenylmethoxy)-2,4-butanetriol]-ethoxy-3-indolyl]-4-3-indolyl)-1H-pyrrole-2,5-dione as a red solid (99% yield).

3-[1-[2-[1-(Triphenylmethoxy)-2,4-butanetriol]-ethoxy-3-indolyl]-4-(3-indolyl)-1H-pyrrole-2,5-dione (10.0 g, 14.2 mmol) was taken up in 100 ml THF and cooled to 0° C. Pyridine (3.45 ml, 42.8 mmol, 3.0 eq) was added and then methanesulfonic anhydride (5.10 g, 28.5 mmol, 2.0 eq). The reaction was allowed to come to room temperature and stirred for 2.5 hours. It was quenched with NH$_4$Cl solution, NaHCO$_3$ solution was added until pH=neutral, and the resulting organic layer was further washed with NH$_4$Cl solution, brine, dried over MgSO$_4$, and evaporated at room temperature (r.t. is important because the product is unstable) to 3-[1-[2-[1-(Triphenylmethoxy)-2,4-methanesulfonyloxy)-butanetriol]-ethoxy-3-indolyl]-4-(3-indolyl)-1H-pyrrole-2,5-dione as a red solid which was carried directly into the next step without further purification. (TY=11.1 g).

3-[1-[2-[1-(Triphenylmethoxy)-2,4-(methanesulfonyloxy)-butanetriol]-ethoxy]-3-indolyl]-4-(3-indolyl)-1H-pyrrole-2,5-dione (4.0 g, 5.12 mmol) was taken up in 80 ml DMF and pyridine (414 μl, 5.12 mmol, 1.0 eq) was added to neutralize any acid formed in the reaction. NaBr (5.26 g, 51.2 mmol, 10.0 eq) was added and the reaction was heated to 50° C. for 3 hours. It was quenched with NH$_4$Cl solution and diluted with EtOAc. The resulting organic layer was washed many times with water to remove DMF, washed with brine, dried over MgSO$_4$, and evaporated to a red residue which was crystallized from acetone/EtOAc to give 3.11 g 3-[1-[2-[1(Triphenylmethoxy)-2,4-(bromo)-butanetriol]-ethoxy]-3-indolyl]-4-(3-indolyl)-1H-pyrrole-2,5-dione as a bright orange solid (79% yield).

Cs$_2$CO$_3$ (213 mg, 0.66 mmol, 1.0 eq) was taken up in 75 ml DMF and heated to 100° C. 3-[1-[2-[1-(Triphenylmethoxy)-2,4-(bromo)-butanetriol]-ethoxy]-3-indolyl]-4-(3-indolyl)-1H-pyrrole-2,5-dione (500 mg, 0.66 mmol) was taken up in 25 ml DMF in a 30 cc syringe pump apparatus. The solution of 3-[1-[2-[1-(Triphenylmethoxy)-2,4-(bromo)-butanetriol]-ethoxy]-3-indolyl]-4-(3-indolyl)-1H-pyrrole-2,5-dione was slowly added to the Cs$_2$CO$_3$ solution at 100° C. over 1 hour. The temperature was maintained for 1 hour after the addition was complete and then the reaction was allowed to come to room temperature. It was quenched by adding NH$_4$Cl solution and diluting with EtOAc. The resulting organic layer was washed several times with water to remove DMF, then washed with brine, dried over MgSO$_4$, and evaporated to a residue that was purified by column chromatography (100%hexane to 1/1 hexane/acetone) to give 328 mg 10,11,14,15-Tetrahydro-13-[(triphenylmethoxy)methyl]-4,9:16,21-dimetheno-1H,13H-dibenzo[E,K]pyrrolo[3,4-H][1,4,13]oxadiaza-cyclohexadecine-1,3-(2H)-dione as a purple solid (73% yield).

EXAMPLE 12

10,11,14.15-Tetrahydro-13-[(dimethylamino)methyl]-4,9:16.21-dimetheno-1H,13H-dibenzo[E,K]pyrrolo[3,4-H]1,4,13]oxadiaza-cylohexadecine-1,3-(2H)-dione 10,11,14,15-Tetrahydro-13-[(triphenylmethoxy)methyl]-4,9:16,21-dimetheno-1H,13H-dibenzo[E,K]pyrrolo[3,4-H][1,4,13]oxadiaza-cyclohexadecine-1,3-(2H)-dione is deprotected to form the free hydroxy and converted to form a bromide. The resulting bromide is deplaced to form the dimethylamine by the addition of dimethylamine in DMF or other techniques appreciated in the art.

The bis-indolylmalimides prepare by the claimed reaction are useful in inhibiting PKC in mammals and treating those conditions associated with PKC abnormalities. The particular dose of the compound administered according to this invention will, of course, be determined by the particular circumstances surrounding the case, including the compound administered, the route of administration, the particular condition being treated, and similar considerations. The compounds can be administered by a variety of routes including the oral, rectal, transdermal, subcutaneous, topical, intravenous, intramuscular or intranasal routes. For all indications, a typical daily dose will contain from about 0.01 mg/kg to about 20 mg/kg of the active compound of this invention. Preferred daily doses will be about 0.05 to about 10 mg/kg, ideally about 0.1 to about 5 mg/kg. However, for topical administration a typical dosage is about 1 to about 500 mg compound per cm$^2$ of an affected tissue. Preferably, the applied amount of compound will range from about 30 to about 300 mg/cm$^2$, more preferably, from about 50 to about 200 mg/cm$^2$, and, most preferably, from about 60 to about 100 mg/cm$^2$.

EXAMPLE 13

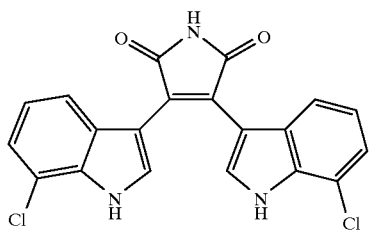

7-chloro-indolyl-3-acetamide (0.10 g) and 0.137 g of 7-chloro-indolyl-3-methylglyoxylate were combined in 3 mL THF under $N_2$. 2.4 mL (5 eq) 1M potassium t-butoxide in THF were added, and the dark reaction mixture stirred one hour at room temperature. Concentrated HCl (1 mL) was added, and the reaction stirred 15 minutes. HPLC indicated 32% of product at 15.29 minutes and 60% undehydrated diasteriomers at 14.43 minutes (see pages 138–139 KUV). Upon reaching reflux there was 77% product and 13% diasteriomers.

After refluxing the reaction mixture one hour, the reaction had converted totally to product. The reaction was allowed to cool and was diluted with 20 mL EtoAc plus 20 mL water. The dried organic layer was evaporated to an oil that was combined using hexanes/EtoAc to give 0.21 g (100%) product that was triturated in $CH_2Cl_2$ to give 0.126 g of a solid.

EXAMPLE 14

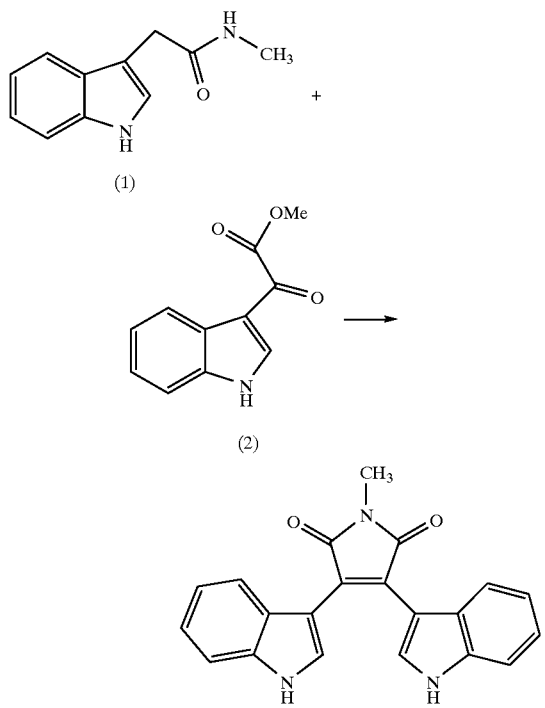

1.0 g (1) and 1.21 g (1.2 eq) (2) were combined in 10 mL THF under $N_2$ and 29.2 mL (5.5 eq) of 1 molar potassium t-butoxide in THF added at room temperature. An orange then dark blue-green mixture resulted that was monitored by HPLC. At time 0 there was still 38.4% (1) and 8% of the product. The reaction was quenched with concentrated HCl after 1.5 hours and stirred overnight (20 hours). 22.3% of the product and 20.2% (1) worked up by extracting with EtoAc (100 mL plus 25 mL).

After washing with 2 times 100 mL water, 25 mL brine, dried ($MgSO_4$) and the reaction mixture was evaporated to give 2.71 g crude material. The crude product was column purified to give 0.38 g (2.1%) RF=0.65 in 4.5/4.5/1 EtoAc/hexanes/MeOH.

The principles, preferred embodiments and modes of operation of the present invention have been described in the foregoing specification. The invention which is intended to be protected herein, however, is not construed to be as limited to the particular forms disclosed, because they are to be regarded as illustrative rather than restrictive. Variations and changes may be made by those skilled in the art without departing from the spirit of the invention.

We claim:

1. A process of preparing compounds of Formula Ia:

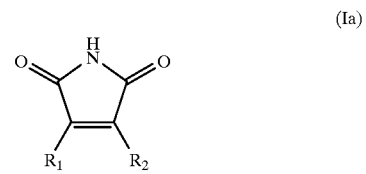

(Ia)

wherein: $R_1$ and $R_2$ independently are optionally substituted 3-indolyl, which comprises, reacting a compound of the formula IV:

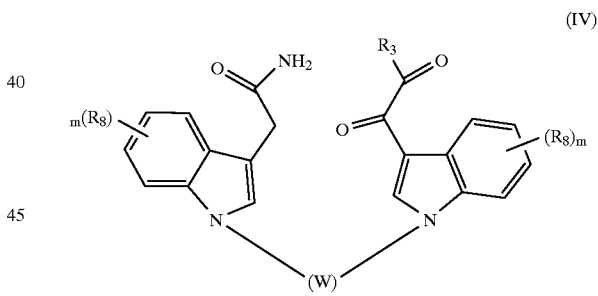

(IV)

wherein:

W represents a $C_4$ to $C_8$ optionally substituted alkylene moiety optionally having an internal ether (—O—), amino (—NH—) or amide (—CONH—) linkage;

$R_3$ is hydrogen, I, Cl, Br, or $OR_4$;

$R_4$ is $C_1$–$C_4$ alkyl;

$R_8$ is hydrogen, $C_1$–$C_4$ alkyl, $C_1$–$C_4$ alkoxy, $(CH_2)_m$ hydroxy, acetyl, carboxy, halo, haloalkyl, nitro, and $(CH_2)_m NR_5R_6$, where $R_5$ and $R_6$ are independently hydrogen, $C_1$–$C_4$ alkyl, phenyl, or benzyl; and m is independently 0, 1, 2, or 3;

in the presence of a base sufficiently strong to deprotonate the amide and methylene at the C-3 position of the indolyl-3-acetamide.

2. The process of claim 1, wherein the compound of formula IV is

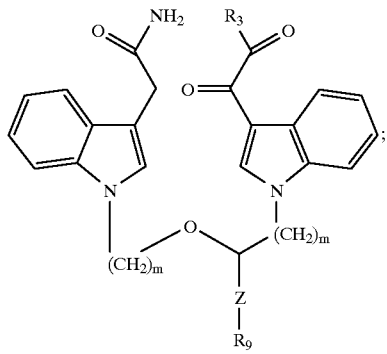

(IVa)

Z is —(CH$_2$)$_p$—;

R$_9$ is halo, protected hydroxy, protected amino, NR$_5$R$_6$, NH(CF$_3$), or N(CH$_3$)(CF$_3$);

R$_5$ and R$_6$ are independently H or C$_1$–C$_4$ alkyl;

p is 0, 1, or 2; and m is independently 2 or 3.

3. The process of claim 2, wherein m is 2 and p is 2.

4. The process of claim 1, wherein the base is selected from the group consisting of alkali metal alkoxides, sodium hydride, lithium diisopropylamide, or n-butyllithium.

5. The process of claim 2, wherein the base is selected from the group consisting of alkali metal alkoxides, sodium hydride, lithium diisopropylamide, or n-butyllithium.

* * * * *